(12) United States Patent
Canzolino

(10) Patent No.: US 8,409,092 B2
(45) Date of Patent: Apr. 2, 2013

(54) MEDICAL IMAGING SYSTEM THAT REDIRECTS HEAT WASTE FOR PATIENT PALLET HEATING

(75) Inventor: Michelle Canzolino, Evanston, IL (US)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 288 days.

(21) Appl. No.: 12/946,498

(22) Filed: Nov. 15, 2010

(65) Prior Publication Data

US 2012/0123237 A1    May 17, 2012

(51) Int. Cl.
*A61B 5/00*    (2006.01)
(52) U.S. Cl. ........ 600/306; 600/407; 600/410; 600/437; 600/443
(58) Field of Classification Search .................. 600/306, 600/407, 410, 437, 443
See application file for complete search history.

(56) References Cited

PUBLICATIONS

"Warm blanket decreases deceptive brown fat uptake in PET cancer scans," Medical Imaging, Oct. 1, 2006.
Baba et al., "Comparison of Uptake of Multiple Clinical Radiotracers into Brown Adipose Tissue Under Cold-Stimulated and Nonstimulated Conditions," The Journal of Nuclear Medicine, vol. 48, No. 10, Oct. 2007, pp. 1715-1723.

*Primary Examiner* — Unsu Jung
*Assistant Examiner* — Joel Lamprecht
(74) *Attorney, Agent, or Firm* — Oblon, Spivak, McClelland, Maier & Neustadt, L.L.P.

(57) ABSTRACT

According to certain embodiments, a medical imaging system includes an imager, a patient pallet, and a heating subsystem. The imager obtains measurement data of a patient. Further, the imager includes at least one electrical component that generates heat. The patient pallet supports the patient to be scanned by the imager. Further, the heating subsystem heats the patient pallet using the heat generated by the at least one electrical component of the imager.

6 Claims, 3 Drawing Sheets

MEDICAL IMAGING SYSTEM THAT REDIRECTS HEAT WASTE FOR PATIENT PALLET HEATING

BACKGROUND OF THE INVENTION

1. Field

Embodiments described herein relate generally to a system for reusing heat generated from one or more electrical components of a device. Specifically, embodiments described herein relate generally to reusing heat generated from one or more electrical components of a medical device such as an imager.

2. Background

Modern medical devices such as imagers including Positron Emission Tomography (PET), Computed Tomography (CT), and Magnetic Resonance (MR) scanners generate a substantial amount of heat waste during operation. This heat waste must be dissipated from the devices in order to prevent overheating. Failure to properly dispose of the heat waste results in overheating, which may lead to premature device failure or malfunction. Typically, this heat waste is dissipated from the devices into the surrounding environment.

PET imaging is growing in the field of medical imaging. PET imaging starts with the administration of a radiopharmaceutical (e.g., fluorodeoxyglucose, also known as FDG) into a patient. The radiopharmaceutical is mostly injected into the patient, but can also be inhaled or ingested. After administration of the radiopharmaceutical, in time, the physical and bio-molecular properties of the agent will cause it to concentrate at specific locations in the human body. The actual spatial distribution of the agent, the intensity of the point or region of accumulation, and the kinetics of the process from administration to capture to eventually elimination are all elements that may have a clinical significance. During this process, a positron emitter attached to the radiopharmaceutical agent, will emit positrons according to the physical properties of the isotope, such as half-life, branching ratio, etc.

Studies have shown that the radiopharmaceutical accumulates in brown fat deposits, or brown adipose tissue (BAT). Brown fat is one of two types of fat or adipose tissue found in mammals and helps keep the body warm in cold temperatures. The accumulation of the radiopharmaceutical in the brown fat deposits, which increases when the patient is cold, can mimic or mask the appearance of cancer in some patients. Pharmaceuticals such as beta blockers or valium-propranolol can be used to reduce brown fat uptake during PET scans. However, the effect of these pharmaceuticals on the uptake is limited and are not without risks such as possible drug interactions. Another option for reducing the brown fat uptake during the PET scans is to keep the patient warm by using, for example, a warm blanket.

BRIEF DESCRIPTION OF THE DRAWINGS

A more complete appreciation of the disclosed embodiment and many of the attendant advantages thereof will be readily obtained as the same becomes better understood by reference to the following detailed description when considered in connection with the accompanying drawings, wherein.

DETAILED DESCRIPTION

According to certain embodiments, a medical imaging system includes an imager, a patient pallet, and a heating subsystem. The imager obtains measurement data of a patient. Further, the imager includes at least one electrical component that generates and emits heat. The patient pallet supports the patient to be scanned by the imager. Further, the heating subsystem heats the patient pallet using the heat generated by the at least one electrical component of the imager.

Figure 1:
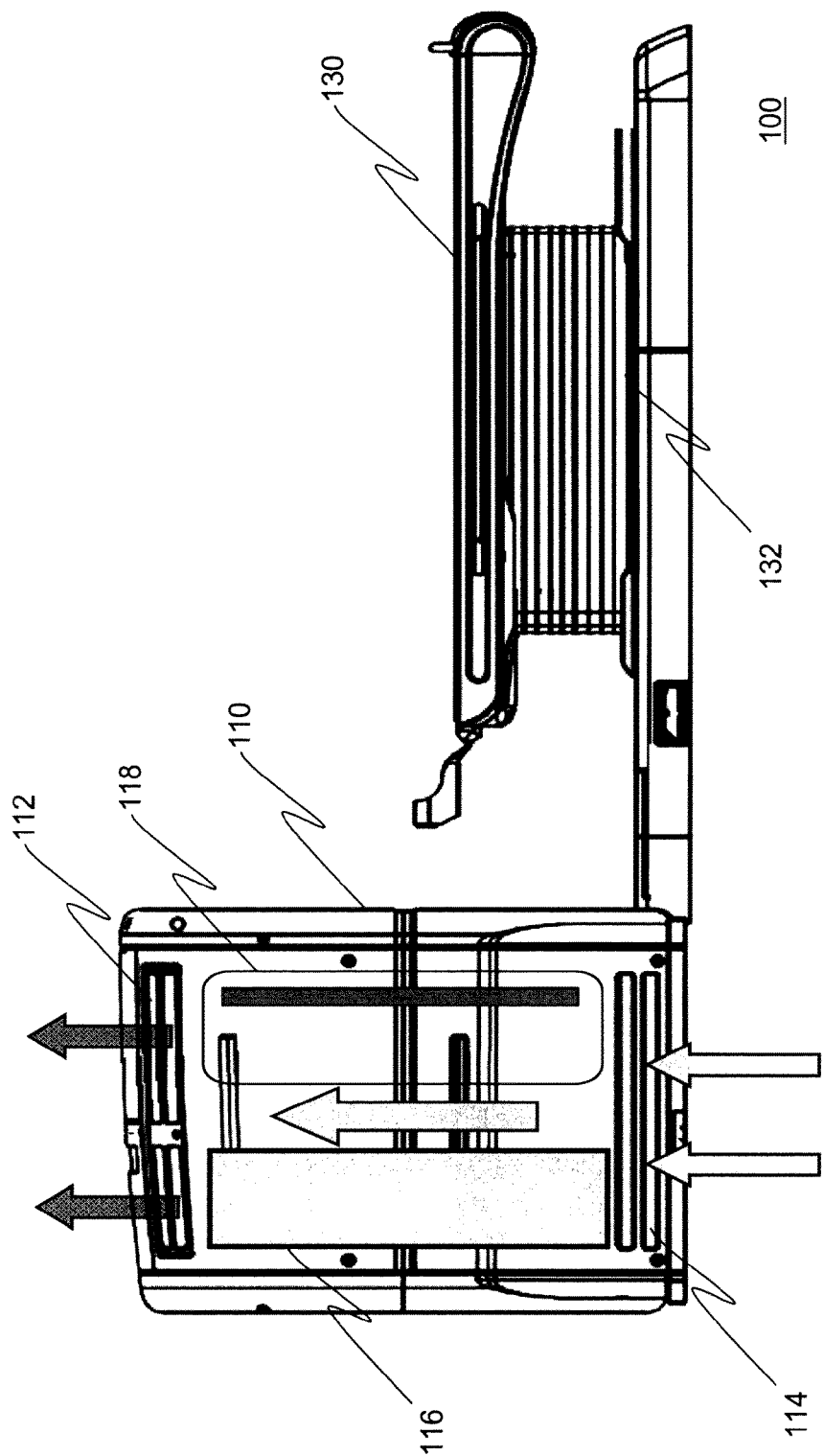
FIG. 1 illustrates a typical air cooled PET imaging system.

FIG. 1 illustrates a PET imaging system 100 that is cooled using a conventional air cooling system. As illustrated in FIG. 1, the PET imaging system 100 includes an assembly 110 on which a PET scanner 116 and an optional scanner (e.g., a CT or MR scanner) 118 are mounted. The PET imaging system 100 further includes a patient pallet 130 that is attached to a base 132. The patient pallet 130 supports a patient to be scanned by the PET imaging system 100. The patient lies flat on the patient pallet 130, which moves incrementally through the PET and/or optional scanners 116, 118.

Typical PET/CT, and PET/MR, scanners dissipate thousands of watts of heat generated by high speed electrical components. This heat must be dissipated to prolong the life of the electrical components and to ensure that the PET imaging system 100 operates normally. Accordingly, as illustrated in FIG. 1, the PET/optional scanners 116, 118 are cooled by, for example, drawing cold air from an imaging room through an intake vent 114 into the assembly 112. The air heated by the PET/optional scanners 116, 118 is then exhausted into the imaging room through the exhaust vent 112.

Since the heated air in the PET imaging system 100 is simply exhausted into the imaging room, the heated air is essentially wasted. The present inventor, however, recognized that the heat generated by the PET/optional scanners 116, 118 could be reused by a heating subsystem to warm up the patient pallet 130 and/or the patient to be scanned. Warming up the patient and/or patient pallet surfaces that the patient is exposed to during scanning not only increases patient comfort, but also has beneficial imaging effects.

The beneficial imaging effects include reduction in brown fat uptake during the PET scans. For example, accumulations of the imaging agent FDG in brown fat deposits, which help keep the body warm in cold temperatures, can mimic or mask the appearance of cancer in up to 9% of patients. Animal trials have suggested that pharmacological interventions can be effective 30% of the time at decreasing brown fat uptake. However, research has shown that a 62% reduction in brown-fat uptake can be achieved by simply keeping the patient warm before contrast injection and during the uptake phase.

In one embodiment, the PET imaging system runs continuously. Accordingly, the transfer of heat from the PET optional scanners to the patient pallet is also continuous.

Figure 2:
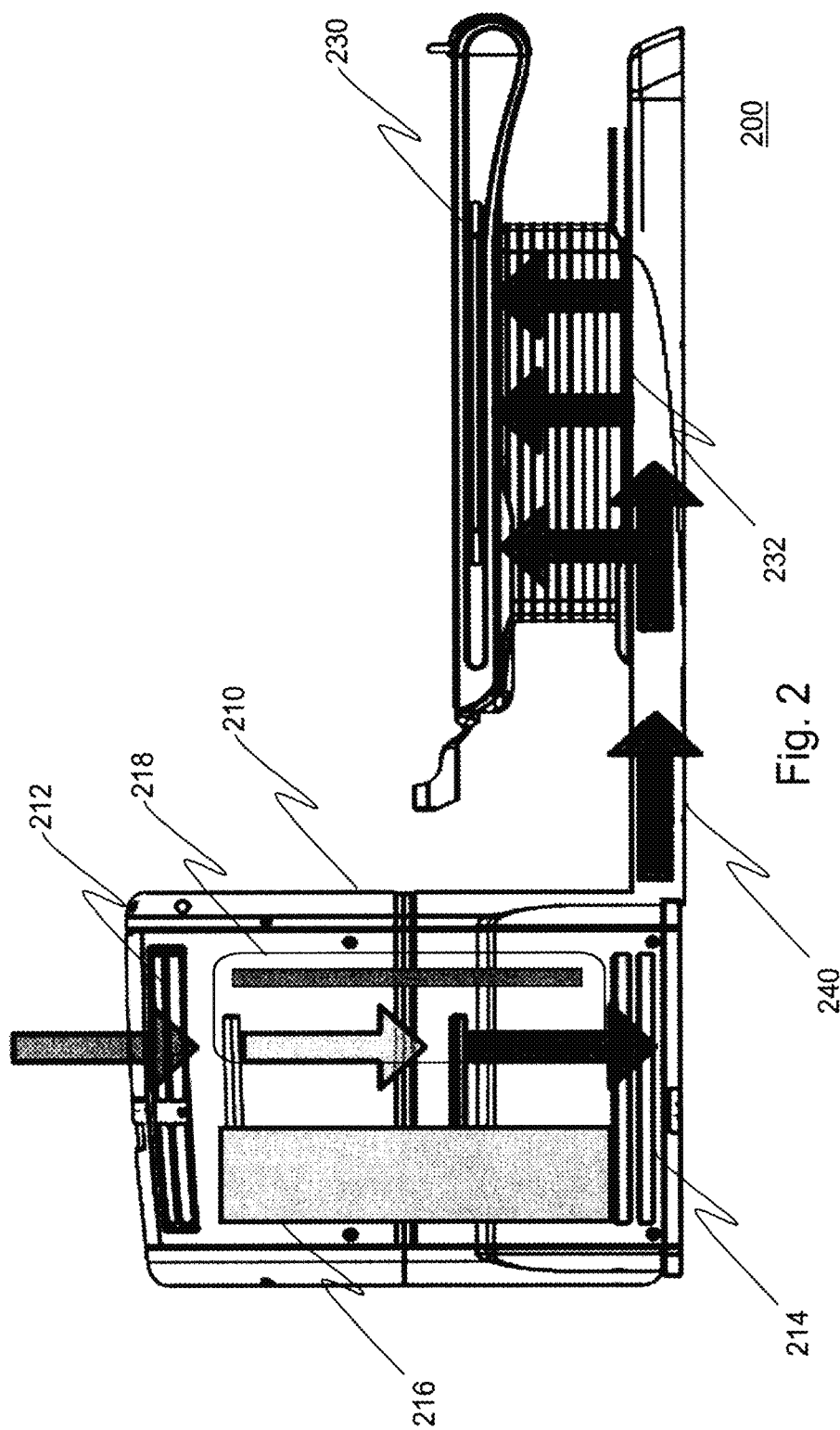
FIG. 2 illustrates an embodiment of a PET imaging system equipped with an air cooling system.

FIG. 2 illustrates a PET imaging system 200 according to one embodiment in which the PET imaging system 200 is equipped with an air cooling system. In one embodiment, the air cooling system functions as a heating subsystem for the patient pallet 230. As illustrated in FIG. 2, cold air is drawn into the assembly 210 through the intake vent 212 to cool the electrical components included in the PET scanner 216 and/or optional scanner 218. The heated air is then exhausted out of the assembly 210 through an air duct 240 and optionally the exhaust vent 214. In one embodiment, the air flow into and out of the assembly 210 is controlled by one or a combination of fans. The air duct 240 connects the assembly 210 and base 232, and is configured to direct the heated air from the assembly 210 to the base 232. Accordingly, in this embodiment, the air cooling system includes at least the one or a combination of fans and the air duct 240. The material used in the air duct 240 is selected such that it does not interfere with the PET/optional scanners 216, 218.

The heated air directed into the base 232 is then used to heat the patient pallet. In one embodiment, the heated air is used to at least warm up surfaces of the patient pallet 230 that could potentially come into contact with the patient. For example, in one embodiment, the heated air is directed inside the body of the patient pallet, or patient bed apparatus, 230 through a flexible duct connected between the patient pallet 230 and the base 232. In this example, the patient pallet 230 includes one or more exhaust ports for allowing the air inside the patient pallet 230 to escape into the imaging room. In a further embodiment, the one or more exhaust ports are configured to direct the heated air onto the patient. For example, the heated air can be vented out of an upper surface of the patient pallet 230 to keep the patient warm. The heated air is vented out of the upper surface through holes or vents formed in, or attached to, the patient pallet 230. Alternatively, air flow (and heat) can be re-directed into specially designed padding that is also used for patient comfort. The padding would then act to distribute the heated air to the patient. Moreover, a blanket could also be used to keep the warmed air to the patient.

Figure 3:
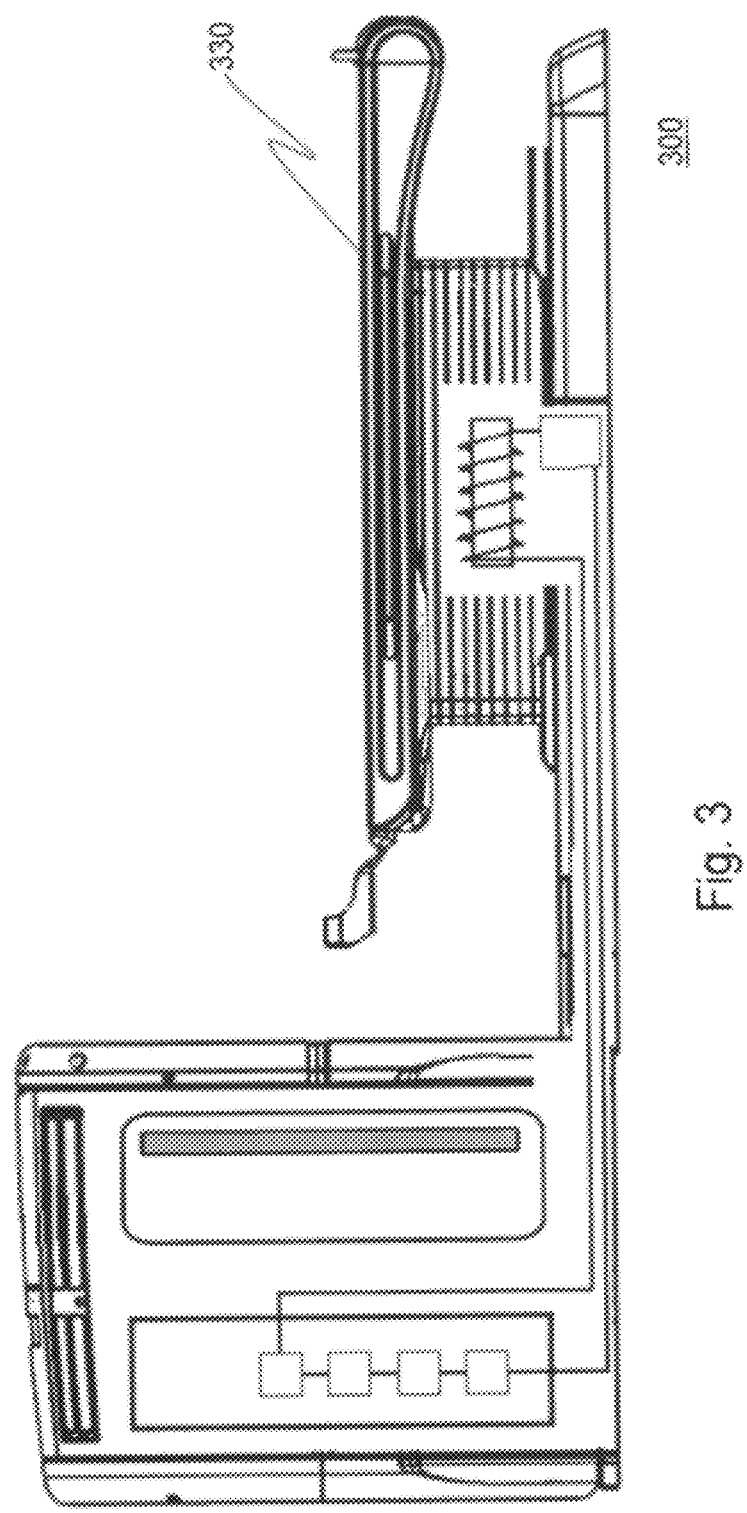
FIG. 3 illustrates an embodiment of a PET imaging system equipped with a fluid cooling system.

FIG. 3 illustrates a PET imaging system 300 according to another embodiment. The PET imaging system 300 is similar to the PET imaging system 200, except for the manner in which the patient pallet 330 is heated. In FIG. 3, the PET imaging system 300 is equipped with a fluid cooling system. In one embodiment, the fluid cooling system functions as a heating subsystem for the patient pallet 330. The fluid used as the coolant may include any one or a combination of liquids, gases, and plasmas.

Although there is little risk that the transfer of heated air or coolant would cause the patient pallet to get too hot, the patient's temperature or the temperature of the patient pallet is measured in one embodiment. Further, in one embodiment, variable speed fans (in the air duct implementation) and an additional exhaust port can easily be used to control the temperature at the point of measurement.

In other embodiments, the patient or patient pallet may be heated by a thermoelectric heating subsystem. In the thermoelectric heating subsystem, heat waste generated by at least one electrical component included in the PET/optional scanners is converted by one or more thermoelectric generators into electrical energy. The converted electrical energy is then used to power heating elements for heating the patient pallet or patient.

Further, although each of the PET imaging systems discussed above are directed to embodiments in which the patient pallet is heated using only the heat generated by the electrical components included in the PET/optional scanners, the disclosed embodiments are not so limited. In another embodiment, the patient pallet can be heated by a source that is independent of the PET/optional scanners. For example, one or more heating elements can be driven by an external power source when the electrical energy generated by the thermoelectric generators is not sufficient.

An imaging system may also use a combination of the heating subsystems discussed above. For example, in one embodiment the imaging system is equipped with both an air and fluid cooling system. In another embodiment, the PET imaging system is equipped with the fluid cooling system of FIG. 3, and one or more thermoelectric generators are attached to the one or more radiators.

Further, although the disclosed embodiments have been discussed with respect to a PET scanner, the disclosed embodiments are not so limited, and are applicable to any medical imaging system in which heat generated by one or more electrical components of a medical device, such as an imager, can be recycled or redirected to increase patient comfort. For example, heat waste generated by at least one electrical component from any one or a combination of imagers (e.g., PET, CT, or MR scanners) can be used to heat a surface that contacts the patient.

While certain embodiments have been described, these embodiments have been presented by way of example only, and are not intended to limit the scope of the invention. Indeed, the novel systems described herein may be embodied in a variety of other forms; furthermore, various omissions, substitutions and changes in the form of the method, computer-readable storage medium, and apparatus described herein may be made without departing from the spirit of the inventions. The accompanying claims and their equivalents are intended to cover such forms or modifications as would fall within the scope and spirit of the inventions.

The invention claimed is:

1. A medical imaging system, comprising:
an imager configured to obtain measurement data of a patient, the imager including at least one electrical component that generates heat;
a patient pallet to support the patient to be scanned by the imager;
a base to support the patient pallet; and
a heating subsystem to heat the patient pallet using the heat generated by the at least one electrical component of the imager.

2. The medical imaging system according to claim 1, wherein the heating subsystem comprises:
a duct to direct air heated by the at least one electrical component from the imager to the patient pallet.

3. The medical imaging system according to claim 1, wherein the heating subsystem comprises:
a fluid block to transfer the heat generated by the at least one electrical component to a fluid;
a radiator disposed within the base to dissipate the heat from the fluid; and
a pump to circulate the fluid between the fluid block and the radiator.

4. The medical imaging system according to claim 1, wherein the heating subsystem comprises:
a thermoelectric generator to convert the heat generated by the at least one electrical component into electrical energy; and
a heater to heat the patient pallet using the electrical energy converted by the thermoelectric generator.

5. The medical imaging system according to claim 1, wherein
the heating subsystem is configured to heat surfaces of the patient pallet that contact the patient.

6. The medical imaging system according to claim 1, wherein
the heating subsystem is configured to provide the heat to the patient pallet continuously.

* * * * *